United States Patent
Lee et al.

(10) Patent No.: US 10,759,912 B2
(45) Date of Patent: Sep. 1, 2020

(54) SUPERABSORBENT POLYMER AND PREPARATION METHOD THEREOF

(71) Applicant: LG Chem, Ltd., Seoul (KR)

(72) Inventors: Soo Jin Lee, Daejeon (KR); Sang Gi Lee, Daejeon (KR); Hye Mi Nam, Daejeon (KR); Min Ho Hwang, Daejeon (KR); Chang Sun Han, Daejeon (KR)

(73) Assignee: LG Chem, Ltd. (KR)

( * ) Notice: Subject to any disclaimer, the term of this patent is extended or adjusted under 35 U.S.C. 154(b) by 209 days.

(21) Appl. No.: 15/752,436

(22) PCT Filed: Apr. 12, 2017

(86) PCT No.: PCT/KR2017/003967
§ 371 (c)(1),
(2) Date: Feb. 13, 2018

(87) PCT Pub. No.: WO2018/084392
PCT Pub. Date: May 11, 2018

(65) Prior Publication Data
US 2019/0010297 A1 Jan. 10, 2019

(30) Foreign Application Priority Data

Nov. 4, 2016 (KR) .................. 10-2016-0146967

(51) Int. Cl.
| C08J 9/228 | (2006.01) |
| C08J 3/24 | (2006.01) |
| C08J 3/12 | (2006.01) |
| C08K 3/22 | (2006.01) |
| C08K 3/26 | (2006.01) |
| C08K 5/00 | (2006.01) |
| C08K 11/00 | (2006.01) |
| A61L 15/60 | (2006.01) |

(52) U.S. Cl.
CPC .............. *C08J 3/245* (2013.01); *C08J 3/122* (2013.01); *C08J 3/126* (2013.01); *C08J 9/228* (2013.01); *C08K 3/22* (2013.01); *C08K 3/26* (2013.01); *C08K 5/0025* (2013.01); *C08K 11/00* (2013.01); *A61L 15/60* (2013.01); *C08J 2205/06* (2013.01); *C08J 2207/12* (2013.01); *C08J 2333/08* (2013.01); *C08J 2333/10* (2013.01); *C08J 2371/00* (2013.01); *C08K 2003/2227* (2013.01); *C08K 2003/262* (2013.01)

(58) Field of Classification Search
CPC ... C08J 3/122; C08J 3/126; C08J 3/245; C08J 9/228; C08J 2205/06; C08J 2207/12; C08J 2333/08; C08J 2333/10; C08J 2371/00; C08K 11/00; C08K 3/22; C08K 3/26; C08K 5/0025; C08K 2003/2227; C08K 2003/262; A61L 15/60
See application file for complete search history.

(56) References Cited

U.S. PATENT DOCUMENTS

| 4,883,478 | A |  | 11/1989 | Lerailler et al. |
| 4,914,170 | A | * | 4/1990 | Chang ..................... A61L 15/60 526/240 |
| 5,145,906 | A |  | 9/1992 | Chambers et al. |
| 6,514,615 | B1 | * | 2/2003 | Sun .......................... A61L 15/60 428/212 |
| 8,697,812 | B2 | * | 4/2014 | Won ....................... B01J 20/267 502/402 |
| 8,945,419 | B2 |  | 2/2015 | Lindner et al. |
| 2003/0118820 | A1 |  | 6/2003 | Sun et al. |
| 2003/0181115 | A1 |  | 9/2003 | Nagasuna et al. |
| 2004/0214946 | A1 | * | 10/2004 | Smith ..................... A61L 15/60 524/556 |
| 2009/0215617 | A1 | * | 8/2009 | Kimura ..................... C08J 3/245 502/402 |
| 2011/0301027 | A1 |  | 12/2011 | Bitis et al. |
| 2013/0175473 | A1 |  | 7/2013 | Wada et al. |
| 2014/0031473 | A1 |  | 1/2014 | Nogi et al. |
| 2014/0312273 | A1 |  | 10/2014 | Wattebled et al. |
| 2015/0093575 | A1 |  | 4/2015 | Naumann et al. |
| 2016/0151531 | A1 |  | 6/2016 | Lee et al. |
| 2016/0271584 | A1 |  | 9/2016 | Lee et al. |
| 2017/0066862 | A1 |  | 3/2017 | Matsumoto et al. |

(Continued)

FOREIGN PATENT DOCUMENTS

| CN | 1365290 A | 8/2002 |
| CN | 105392805 A | 3/2016 |
| EP | 0450924 B1 | 10/1996 |

(Continued)

OTHER PUBLICATIONS

Search report from International Application No. PCT/KR2017/003967, dated Aug. 11, 2017.
Schwalm, R., "UV Coatings; Basics, Recent Developments and New Applications." Elsevier Science, Dec. 21, 2006, p. 115.
Odian, G..G., "Principles of Polymerization." Second Edition, John Wiley & Sons, Inc,, Copyright 1981, p. 203.
Extended European Search Report including Written Opinion for Application No. EP17835443.7 dated Aug. 7, 2018.
Third Party Observation for Application No. PCT/KR2017/003967 dated Mar. 1, 2019.
First Search Report from Chinese Office Action for CN201780003076.1 dated Apr. 8, 2020; 1 page.

*Primary Examiner* — Irina S Zemel
(74) *Attorney, Agent, or Firm* — Lerner, David, Littenberg, Krumholz & Mentlik, LLP

(57) ABSTRACT

Provided are a superabsorbent polymer and a preparation method thereof. The superabsorbent polymer may effectively avoid a rewetting phenomenon after absorbing liquid, because a saline solution hardly remains in the empty spaces between swollen gel particles. Accordingly, the superabsorbent polymer may be used to provide hygienic materials, such as diapers, sanitary napkins, etc., which have a fluffy texture even after body fluid is discharged thereto.

11 Claims, 2 Drawing Sheets

(56) References Cited

U.S. PATENT DOCUMENTS

2017/0073478 A1    3/2017   Joo et al.
2017/0326528 A1   11/2017   Park et al.

FOREIGN PATENT DOCUMENTS

| | | |
|---|---|---|
| EP | 1940948 B1 | 2/2010 |
| EP | 1196204 B2 | 3/2010 |
| EP | 2277557 A1 | 1/2011 |
| EP | 2620465 B1 | 9/2014 |
| EP | 2643392 B1 | 12/2014 |
| EP | 3088446 A1 | 11/2016 |
| JP | 2002165837 A | 6/2002 |
| JP | 2002226599 A | 8/2002 |
| JP | 2007314794 A | 12/2007 |
| JP | 5604444 B2 | 10/2014 |
| KR | 100606390 B1 | 7/2006 |
| KR | 20130097771 A | 9/2013 |
| KR | 20140102264 A | 8/2014 |
| KR | 101507287 B1 | 3/2015 |
| KR | 20150064649 A | 6/2015 |
| KR | 20160004967 A | 1/2016 |
| KR | 20160016714 A | 2/2016 |
| KR | 101635291 B1 | 6/2016 |
| KR | 20160091242 A | 8/2016 |
| KR | 20170112856 A | 10/2017 |
| WO | 87003208 A1 | 6/1987 |
| WO | 2004096304 A1 | 11/2004 |
| WO | 2005044900 A1 | 5/2005 |
| WO | 2012102407 A1 | 8/2012 |
| WO | 2015133440 A1 | 9/2015 |

* cited by examiner

[FIG. 1]
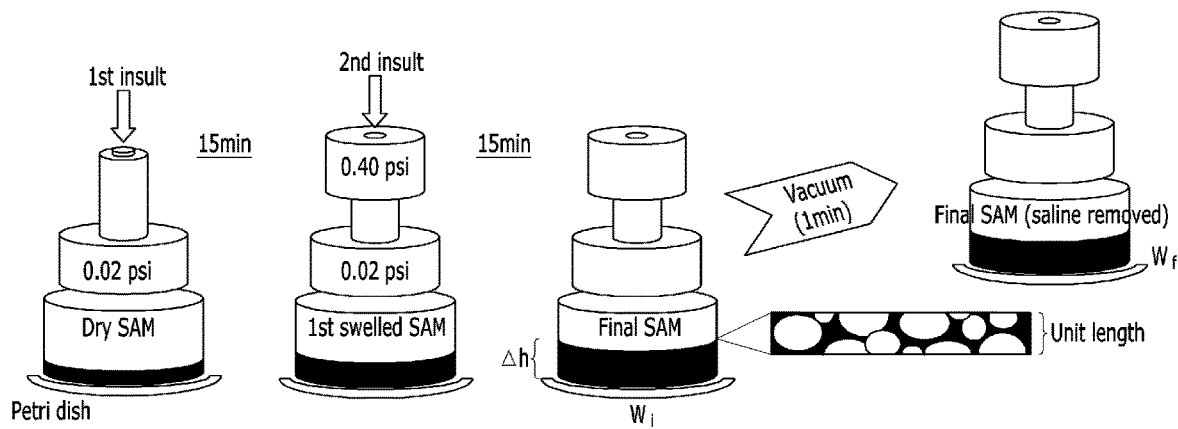
[FIG. 2]
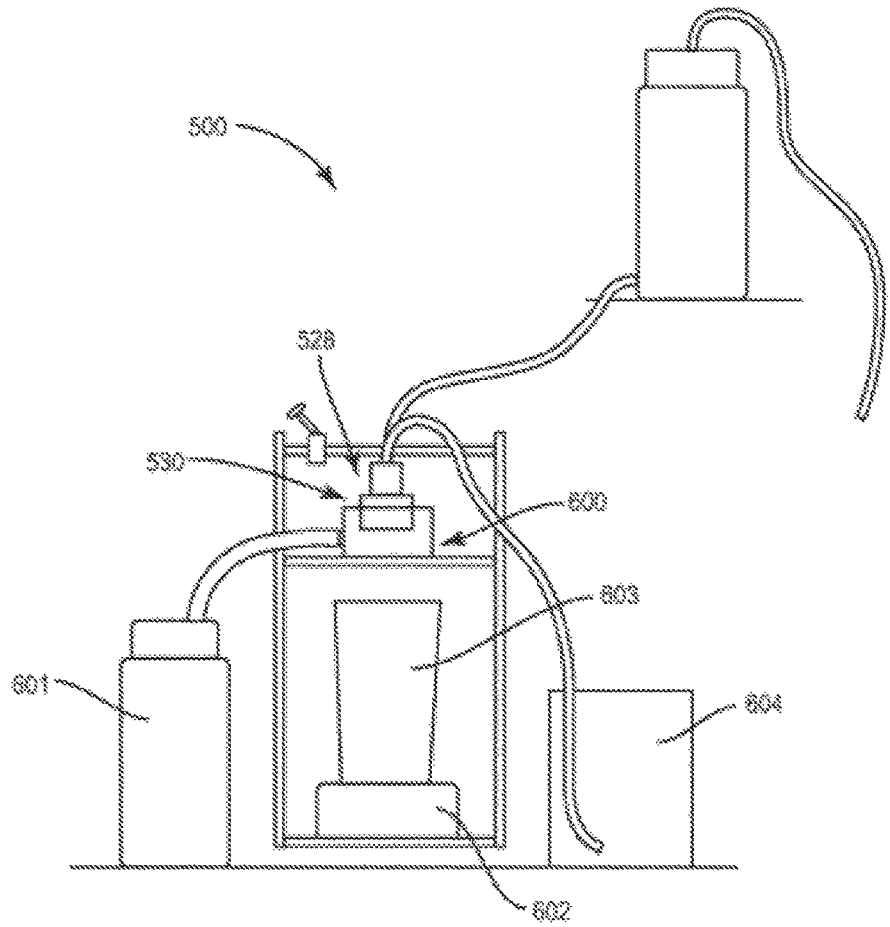

[FIG. 3]
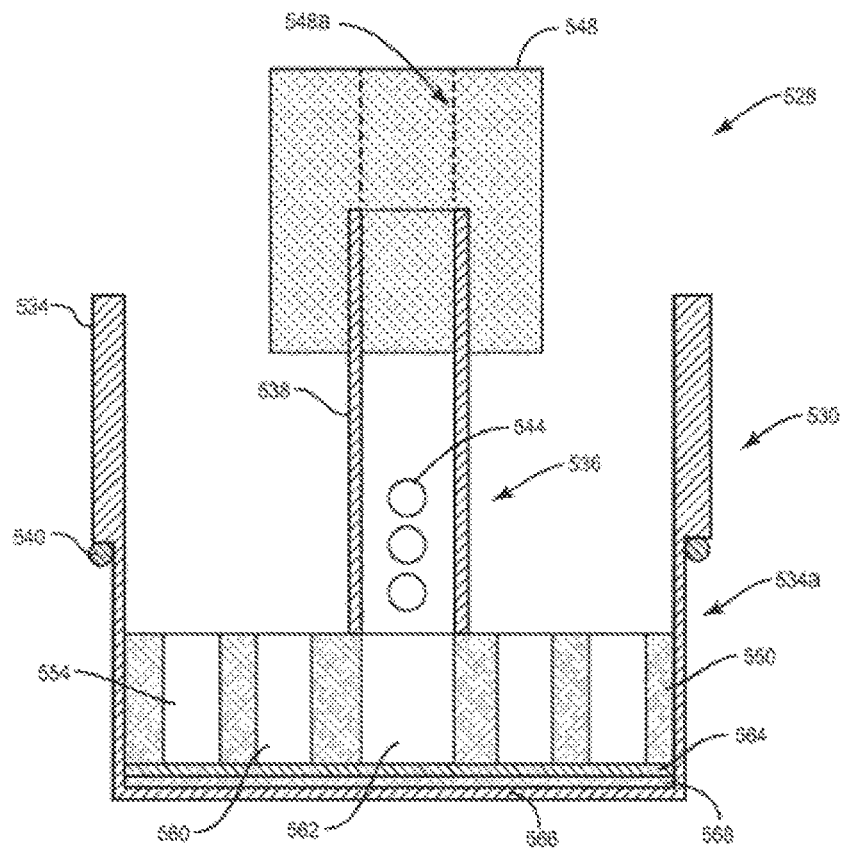
[FIG. 4]
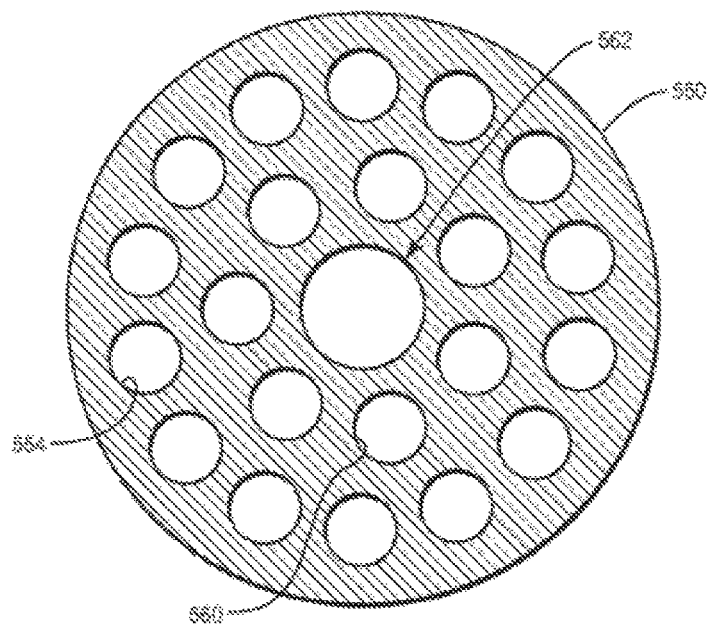

SUPERABSORBENT POLYMER AND PREPARATION METHOD THEREOF

CROSS-REFERENCE TO RELATED APPLICATION

The present application is a national phase entry under 35 U.S.C. § 371 of International Application No. PCT/KR2017/003967 filed on Apr. 12, 2017, which claims priority from of Korean Patent Application No. 10-2016-0146967, filed with Korean Intellectual Property Office on Nov. 4, 2016, the entire contents of which are incorporated herein by reference.

TECHNICAL FIELD

The present invention relates to a superabsorbent polymer having a remarkably improved anti-rewetting effect, and a preparation method thereof.

BACKGROUND ART

A superabsorbent polymer (SAP) is a synthetic polymeric material capable of absorbing moisture from about 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, sanitary napkins, etc., but also for water retaining soil products for gardening, water stop materials for the civil engineering and construction, sheets for raising seedling, fresh-keeping agents for food distribution fields, materials for poultice, etc.

In most cases, these superabsorbent polymers have been widely used in the field of hygienic materials such as diapers, sanitary napkins, etc. For these applications, superabsorbent polymers are required to exhibit high absorbency with respect to moisture, etc., must not release absorbed water even under an external pressure, and also must maintain the shape under volume expansion (swelling) due to water absorption to show excellent permeability.

Reportedly, it is difficult to improve centrifuge retention capacity (CRC), which is a basic physical property of showing water absorption and retention capacities of the superabsorbent polymer, and absorbency under load (AUL), which is a property of retaining absorbed water even under an external pressure, at the same time. The reason is that when the overall crosslinking density of the superabsorbent polymer is controlled to be low, centrifuge retention capacity becomes relatively high, but a crosslinking structure becomes loose and gel strength becomes low, leading to a reduction in absorbency under load. On the contrary, when the crosslinking density is controlled to be high, and therefore absorbency under load is improved, water is hardly absorbed between compact crosslinking structures, leading to a reduction in basic centrifuge retention capacity. Because of the above-described reasons, there have been limitations in providing superabsorbent polymers in which centrifuge retention capacity and absorbency under load are improved at the same time.

However, superabsorbent polymers have been required to have higher absorption performances with recent slimness of sanitary materials such as diapers, sanitary napkins, etc. Of them, simultaneous enhancement of centrifuge retention capacity and absorbency under load which are incompatible physical properties, and improvement of liquid permeability are emerging as important issues.

Further, a pressure by a user's weight may be applied to sanitary materials such as diapers, sanitary napkins, etc. In particular, when liquid is absorbed by the superabsorbent polymer used in sanitary materials such as diapers, sanitary napkins, etc., and then a pressure by a user's weight is applied thereto, a rewetting phenomenon may occur, in which the rewetting phenomenon causes the superabsorbent polymer to release part of the absorbed liquid again. Therefore, to avoid this rewetting phenomenon, many attempts have been made to improve absorbency under load, liquid permeability, etc. However, a specific method capable of effectively avoiding the rewetting phenomenon has not been suggested yet.

DISCLOSURE

Technical Problem

The present invention provides a superabsorbent polymer capable of effectively avoiding a rewetting phenomenon after absorbing liquid, thereby providing a fluffy texture.

Further, the present invention provides a method of preparing the superabsorbent polymer.

Technical Solution

According to an embodiment of the present invention, provided is a superabsorbent polymer including a base resin powder including a crosslinked polymer which is prepared by crosslinking polymerization of water-soluble ethylene-based unsaturated monomers having at least partially neutralized acidic groups in the presence of an internal crosslinking agent; and a surface-crosslinked layer formed on the base resin powder, in which the surface-crosslinked layer is obtained by additionally crosslinking the crosslinked polymer in the presence of a surface crosslinking agent, and having SE (saline extracted) of 0.05%/mm or less, as calculated by the following Equation 1:

$$SE = \frac{\Delta w}{w_t \times h} \times 100 \qquad [\text{Equation 1}]$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which may uniformly provide a load of 0.02 psi is put thereon, 20 g of a physiological saline solution (0.9% by weight of a sodium chloride aqueous solution) is injected into the inlet of the piston, and 15 minutes later, a piston which may uniformly provide a load of 0.40 psi is additionally put thereon, 20 g of the physiological saline solution is additionally injected into the inlet of the piston, and 15 minutes later, the height of the swollen superabsorbent polymer is measured, $w_t$ represents a total weight (g) of the physiological saline solution injected into the superabsorbent polymer, and $\Delta w$ represents a weight change (g) before and after extraction, which is calculated by extracting the physiological saline solution from the swollen superabsorbent polymer for 1 minute under vacuum of 5 psi by using a vacuum pump, after measuring the height of the swollen superabsorbent polymer.

Centrifuge retention capacity (CRC) of the superabsorbent polymer in a physiological saline solution may be 31 g/g to 40 g/g.

Absorbency under load (AUL) of 0.9 psi of the superabsorbent polymer in the physiological saline solution may be 19 g/g to 25 g/g.

Free swell gel bed permeability (GBP) of the superabsorbent polymer in the physiological saline solution may be 40 darcy to 60 darcy.

A vortex time of the superabsorbent polymer may be 40 sec to 60 sec.

Meanwhile, according to another embodiment of the present invention, provided is a method of preparing the superabsorbent polymer, the method including the steps of: performing crosslinking polymerization of a monomer mixture including water-soluble ethylene-based unsaturated monomers having at least partially neutralized acidic groups, in the presence of an internal crosslinking agent to form a water-containing gel polymer; drying, pulverizing, and size-sorting the water-containing gel polymer to form a base resin powder; and additionally crosslinking the surface of the base resin powder in the presence of a surface crosslinking agent to form a surface-crosslinked layer, wherein in the step of forming the water-containing gel polymer, the internal crosslinking agent is used in an amount of 0.1 parts by weight to 0.5 parts by weight, based on 100 parts by weight of the water-soluble ethylene-based unsaturated monomers before neutralization of the acidic groups of the monomers having the acidic groups included in the water-soluble ethylene-based unsaturated monomers, in the step of forming the surface-crosslinked layer, a heating time taken to heat from a temperature of 60° C. to 80° C. to a temperature of 180° C. to 200° C. is controlled from 5 min to 1 hr, and the temperature is maintained at 180° C. to 200° C. for 10 min to 40 min while heating the base resin powder, in the step of forming the surface-crosslinked layer, alumina is added, or after the step of forming the surface-crosslinked layer, alumina is added, or in the step of forming the surface-crosslinked layer, alumina is added and after the step of forming the surface-crosslinked layer, alumina is further added, thereby preparing the superabsorbent polymer having SE of 0.05%/mm or less, as calculated by Equation 1.

In the step of forming the water-containing gel polymer, the monomer mixture may further include, as a foaming agent, one or more carbonates selected from the group consisting of magnesium carbonate, calcium carbonate, sodium bicarbonate, sodium carbonate, potassium bicarbonate, and potassium carbonate.

In the step of forming the water-containing gel polymer, the monomer mixture may further include, as a surfactant, one or more selected from the group consisting of alkyl sulfate salts having 8 to 24 carbon atoms and sugar ester-based surfactants.

The base resin powder prepared by the step of forming the base resin powder may have centrifuge retention capacity (CRC) of 34 g/g to 35.8 g/g in the physiological saline solution.

In the step of forming the surface-crosslinked layer, a heating time taken to heat from a reactant temperature of 60° C. to 80° C. to a reactor temperature of 180° C. to 200° C. is controlled from 5 min to 1 hr, and the reactor temperature is maintained at 180° C. to 200° C. for 10 min to 40 min.

Meanwhile, according to still another embodiment of the present invention, provided is a superabsorbent polymer including a base resin powder including a crosslinked polymer which is prepared by crosslinking polymerization of water-soluble ethylene-based unsaturated monomers having at least partially neutralized acidic groups in the presence of an internal crosslinking agent; and a surface-crosslinked layer formed on the base resin powder, in which the surface-crosslinked layer is obtained by additionally crosslinking the crosslinked polymer in the presence of a surface crosslinking agent, and having absorbency under load (AUL) of 0.9 psi of 19 g/g to 25 g/g in a physiological saline solution and SE (saline extracted) of 0.05%/mm or less, as calculated by the following Equation 1:

$$SE = \frac{\Delta w}{w_t \times h} \times 100 \qquad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which may uniformly provide a load of 0.02 psi is put thereon, 20 g of a physiological saline solution (0.9% by weight of a sodium chloride aqueous solution) is injected into the inlet of the piston, and 15 minutes later, a piston which may uniformly provide a load of 0.40 psi is additionally put thereon, 20 g of the physiological saline solution is additionally injected into the inlet of the piston, and 15 minutes later, the height of the swollen superabsorbent polymer is measured, $w_t$ represents a total weight (g) of the physiological saline solution injected into the superabsorbent polymer, and $\Delta w$ represents a weight change (g) before and after extraction, which is calculated by extracting the physiological saline solution from the swollen superabsorbent polymer for 1 minute under vacuum of 5 psi by using a vacuum pump, after measuring the height of the swollen superabsorbent polymer.

Effect of the Invention

In a superabsorbent polymer according to an embodiment of the present invention, a saline solution hardly remains in the empty spaces between swollen gel particles, thereby effectively preventing a rewetting phenomenon after liquid is absorbed. Accordingly, the superabsorbent polymer may be used to provide hygienic materials, such as diapers, sanitary napkins, etc., which have a fluffy texture even after body fluid is discharged thereto.

BRIEF DESCRIPTION OF DRAWINGS

FIG. 1 is a schematic view of an exemplary apparatus for measuring % saline extracted (SE) from the empty spaces between swollen superabsorbent polymer particles, and a measurement method thereof; and FIGS. 2 to 4 are schematic views of an exemplary apparatus for measuring gel bed permeability and components provided in the apparatus.

DETAILED DESCRIPTION OF THE EMBODIMENTS

Hereinafter, a superabsorbent polymer and a preparation method thereof according to specific embodiments of the present invention will be described.

According to an embodiment of the present invention, provided is a superabsorbent polymer including a base resin powder including a crosslinked polymer which is prepared by crosslinking polymerization of water-soluble ethylene-based unsaturated monomers having at least partially neutralized acidic groups in the presence of an internal crosslinking agent; and a surface-crosslinked layer formed on the base resin powder, in which the surface-crosslinked layer is obtained by additionally crosslinking the crosslinked polymer in the presence of a surface crosslinking agent, and having SE (saline extracted) of 0.05%/mm or less, as calculated by the following Equation 1:

$$SE = \frac{\Delta w}{w_t \times h} \times 100 \qquad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which may uniformly provide a load of 0.02 psi is put thereon, 20 g of a physiological saline solution (0.9% by weight of a sodium chloride aqueous solution) is injected into the inlet of the piston, and 15 minutes later, a piston which may uniformly provide a load of 0.40 psi is additionally put thereon, 20 g of the physiological saline solution is additionally injected into the inlet of the piston, and 15 minutes later, the height of the swollen superabsorbent polymer is measured, $w_t$ represents a total weight (g) of the physiological saline solution injected into the superabsorbent polymer, and $\Delta w$ represents a weight change (g) before and after extraction, which is calculated by extracting the physiological saline solution from the swollen superabsorbent polymer for 1 minute under vacuum of 5 psi by using a vacuum pump, after measuring the height of the swollen superabsorbent polymer.

The experimental results of the present inventors confirmed that a rewetting phenomenon of the superabsorbent polymer depends on the amount of saline remaining in the empty spaces between swollen gel particles, and when the amount of the saline remaining in the empty spaces between swollen gel particles is minimized, basic physical properties of the superabsorbent polymer are improved and the rewetting phenomenon is effectively prevented.

In particular, when % saline extracted (SE) from the empty spaces between the swollen superabsorbent polymer particles is 0.05%/mm or less, as calculated by Equation 1, the superabsorbent polymer may exhibit excellent absorption properties and superior anti-rewetting effect. A more detailed description of a method of measuring SE may refer to Experimental Example below.

The superabsorbent polymer having the above SE value may exhibit balanced centrifuge retention capacity, absorbency under load, liquid permeability, etc., such that the saline rarely remains in the empty spaces between gel particles under a swollen state.

For example, centrifuge retention capacity (CRC) of the superabsorbent polymer in a physiological saline solution may be 31 g/g to 40 g/g, 31 g/g to 35 g/g, or 31 g/g to 33 g/g. Absorbency under load (AUL) of 0.9 psi of the superabsorbent polymer in a physiological saline solution may be 19 g/g to 25 g/g, 19 g/g to 23 g/g, or 19 g/g to 21 g/g. Free swell gel bed permeability (GBP) of the superabsorbent polymer in a physiological saline solution may be 40 darcy to 60 darcy, 50 darcy to 60 darcy, or 53 darcy to 57 darcy. A vortex time of the superabsorbent polymer may be 40 sec to 60 sec, 40 sec to 55 sec or 45 sec to 50 sec.

The superabsorbent polymer may exhibit the above-described CRC, AUL, GBP, and vortex time at the same time. Such a superabsorbent polymer having the balanced absorption properties absorbs a large amount of saline very rapidly and well retains the absorbed saline even under an external pressure while showing excellent liquid permeability. As a result, the saline hardly remains in the empty spaces between the swollen gel particles of the superabsorbent polymer. Accordingly, the superabsorbent polymer may effectively avoid the rewetting phenomenon, in which the rewetting phenomenon causes the absorbed saline to leak back out by an external pressure, thereby providing hygienic materials, such as diapers, sanitary napkins, etc., which have a fluffy texture even after body fluid is discharged thereto.

Meanwhile, in the present description, psi is mainly used as a pressure unit. 1 psi is 6,894.73326 Pa (N/m$^2$), and a pressure expressed as psi may be converted to Pa which is the SI unit for pressure.

The centrifuge retention capacity (CRC) in the physiological saline solution may be measured in accordance with EDANA method WSP 241.2. More specifically, the centrifuge retention capacity may be calculated by the following Calculation Formula 1, after size-sorting the superabsorbent polymer to prepare a superabsorbent polymer having a particle size of 150 μm to 850 μm, and allowing the superabsorbent polymer to absorb the physiological saline solution over 30 minutes:

CRC (g/g)={[$W_2$(g)−$W_1$(g)]/$W_0$(g)}−1  [Calculation Formula 1]

wherein $W_0$(g) represents an initial weight (g) of the superabsorbent polymer having a particle size of 150 μm to 850 μm, $W_1$(g) represents a weight of an empty non-woven fabric bag, which was measured after immersing the empty non-woven fabric bag containing no superabsorbent polymer in 0.9% by weight of a physiological saline solution at room temperature for 30 minutes, and dehydrating the non-woven fabric bag using a centrifuge at 250 G for 3 minutes, and $W_2$(g) represents a weight of a non-woven fabric bag containing a superabsorbent polymer having a particle size of 150 μm to 850 μm, which was measured after immersing the non-woven fabric bag containing the superabsorbent polymer in 0.9% by weight of a physiological saline solution at room temperature for 30 minutes, and dehydrating the non-woven fabric bag using a centrifuge at 250 G for 3 minutes.

Further, the absorbency under load (AUL) of 0.9 psi may be measured in accordance with EDANA method WSP 242.2. More specifically, the absorbency under load may be calculated by the following Calculation Formula 2, after allowing the superabsorbent polymer to absorb a physiological saline solution under a pressure of about 0.9 psi over 1 hr:

AUL (g/g)=[$W_4$(g)−$W_3$(g)]/$W_0$(g)  [Calculation Formula 2]

wherein $W_0$(g) represents an initial weight (g) of the superabsorbent polymer, $W_3$(g) represents the sum of the weight of the superabsorbent polymer and a weight of an apparatus capable of providing a load for the superabsorbent polymer, and $W_4$(g) represents the sum of the weight of the superabsorbent polymer after allowing the superabsorbent polymer to absorb the physiological saline solution under a load (0.9 psi) for 1 hour, and the weight of the apparatus capable of providing the load for the superabsorbent polymer.

$W_0(g)$ described in Calculation Formulae 1 and 2 represents the initial weight (g) of the superabsorbent polymer before allowing the superabsorbent polymer to absorb the physiological saline solution, and may be the same as or different from each other.

The gel bed permeability (GBP) in the physiological saline solution may be measured in a unit of Darcy or $cm^2$ in accordance with the following method described in Patent Application No. 2014-7018005. 1 darcy means that a fluid of 1 cp viscosity flows 1 mm per sec through 1 $cm^2$ under a pressure gradient of 1 atm per 1 cm. The gel bed permeability has the same units as area, and 1 darcy is equal to $0.98692 \times 10^{-12}$ $m^2$ or $0.98692 \times 10^{-8}$ $cm^2$.

More specifically, GBP, as used herein, means a degree of penetration (or permeability) of a swollen gel layer (or bed) under what is commonly referred to as a free swell state of 0 psi (Gel Bed Permeability (GBP) Under 0 psi Swell Pressure Test), and may be measured by using an apparatus shown in FIGS. 2 to 4.

Referring to FIGS. 2 to 4, in an apparatus 500 for measuring GBP, a test apparatus assembly 528 includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm. The plunger head 550 has a concentric inner ring of seven holes 560 and an outer ring of 14 holes 554, all holes having a diameter of about 8.8 mm as well as a hole of about 16 mm aligned with the shaft. The plunger head 550 is machined from a LEXAN rod or equivalent material and has a height of about 16 mm and a diameter sized such that it fits within the cylinder 534 with minimum wall clearance but still slides freely. The total length of the plunger head 550 and shaft 538 is about 8.25 cm, but may be machined at the top of the shaft to obtain the desired mass of the plunger 536. The plunger 536 includes a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. The sample container 530 includes a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) may be suitably used. A gel particle sample (swollen superabsorbent polymer), indicated as 568 in FIG. 3, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 $cm^2$), a wall thickness of about 0.5 cm and a height of about 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

An annular weight 548 has a counter-bored hole about 2.2 cm in diameter and 1.3 cm deep so that it slips freely onto the shaft 538. The annular weight also has a thru-bore 548a of about 16 mm. The annular weight 548 may be made from stainless steel or from other suitable materials resistant to corrosion by a physiological saline solution (0.9% by weight of a sodium chloride aqueous solution). The combined weight of the plunger 536 and annular weight 548 equals about 596 g, which corresponds to a pressure applied to the sample 568 of about 0.3 psi, or about 20.7 $dynes/cm^2$ (2.07 kPa), over a sample area of about 28.27 $cm^2$.

When a test solution flows through the test apparatus during GBP testing, the sample container 530 generally rests on a weir 600. The purpose of the weir is to divert liquid that overflows the top of the sample container 530 and diverts the overflow liquid to a separate collection device 601. The weir may be positioned above a scale 602 with a beaker 603 resting on it to collect a physiological saline solution passing through the swollen sample 568.

To conduct the gel bed permeability test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 N. It is important to measure each empty sample container 530 and to keep track of which plunger 536 and weight 548 are used when using a multiple test apparatus.

Further, it is desirable that a base on which the sample container 530 is placed is level, and the top surface of the weight 548 is parallel to the bottom surface of the sample container 530. A test sample is prepared from a superabsorbent polymer to be tested for GBP. For example, a superabsorbent polymer having a particle size of about 300 µm to about 600 µm, which is prescreened through a US standard 30 mesh screen and retained on a US standard 50 mesh screen, is prepared as the test sample. About 2.0 g of the sample is placed in the sample container 530 and spread out evenly on the bottom of the sample container. The container, with 2.0 g of sample in it, without the plunger 536 and weight 548 therein, is then submerged in the physiological saline solution for about 60 minutes to allow the sample to swell free of any restraining load. At this time, the sample container 530 is set on a mesh located in a liquid reservoir so that the sample container 530 is raised slightly above the bottom of the liquid reservoir. The mesh does not inhibit the flow of the physiological saline solution into the sample container 530. The mesh may be a mesh as part number 7308 from Eagle Supply and Plastic (having a place of business in Appleton, Wis., USA). During saturation, a depth of the physiological saline solution may be controlled such that the surface within the sample container is defined solely by the sample, rather than the physiological saline solution.

At the end of this period, an assembly of the plunger 536 and the weight 548 is placed on the saturated sample 568 in the sample container 530 and then the sample container 530, plunger 536, weight 548, and sample 568 are removed from the solution. Then, before GBP measurement, the sample container 530, plunger 536, weight 548, and sample 568 are to remain at rest for about 30 seconds on a large grid non-deformable plate of uniform thickness. The plate will prevent liquid in the sample container from being released onto a flat surface due to surface tension. The plate has an overall dimension of 7.6 cm×7.6 cm, and each grid has a size dimension of 1.59 cm long×1.59 cm wide×1.12 cm deep. A material suitable for the plate is a parabolic diffuser panel, catalogue number 1624K27, available from McMaster Carr Supply Company (having a place of business in Chicago, Ill., USA), which may then be cut to the proper dimensions.

The height from the top of the weight 548 to the bottom of the sample container 530 is measured again by using the same thickness gauge used previously, provided that the zero point is unchanged from the initial height measurement. The height measurement should be made as soon as practicable after the thickness gauge is engaged. The height measurement of the empty assembly where the plunger 536 and the weight 548 are placed in the empty sample container 530 is subtracted from the height measurement obtained after saturating the sample 568. The resulting value is the thickness or height "H" of the saturated sample 568. Further, if the plate is contained in the assembly containing the saturated sample 568, this plate must also be present upon measuring the height of the empty assembly.

The GBP measurement is initiated by delivering a flow of a physiological saline solution into the sample container 530 with the saturated sample 568, plunger 536, and weight 548 inside. The flow rate of the physiological saline solution into the container is adjusted to cause the physiological saline solution to overflow the top of the cylinder 534, resulting in a consistent head pressure equal to the height of the sample container 530. The physiological saline solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using a scale 602 and a beaker 603. Data points from the scale 602 are collected every second for at least 60 seconds once the overflow has begun. Data collection may be taken manually or with data collection software. The flow rate, Q through the swollen sample 568 is determined in units of g/sec by a linear least-square fit of fluid (g) passing through the sample 568 versus time (sec).

GBP ($cm^2$) may be calculated from the obtained data according to the following Calculation Formula 3 to confirm gel bed permeability:

$$K=[Q*H*\mu]/[A*\rho*P]$$ [Calculation Formula 3]

wherein K is gel bed permeability ($cm^2$),

Q is a flow rate (g/sec),

H is a height of a sample (cm), $\mu$ is liquid viscosity (p) (viscosity of the test solution to be used in this test is about 1 cp), A is a cross-sectional area for liquid flow (28.27 $cm^2$ for the sample container used in this test), $\rho$ is a liquid density ($g/cm^3$) (about 1 $g/cm^3$ for the test solution used in this test), and P is a hydrostatic pressure ($dynes/cm^2$) (normally about 7,797 $dynes/cm^2$).

The hydrostatic pressure is calculated from $P=\rho*g*h$, wherein $\rho$ is a liquid density ($g/cm^3$), g is gravitational acceleration (nominally 981 $cm/sec^2$), and h is a fluid height (e.g., 7.95 cm for the GBP test described herein).

The vortex time may be measured in seconds in accordance with a method described in International Patent Application No. 1987-003208. More specifically, the vortex time may be calculated by measuring a time in seconds which is required until the vortex disappears, after adding 2 g of the superabsorbent polymer to 50 mL of a physiological saline solution and then agitating it at 600 rpm.

Meanwhile, according to another embodiment of the present invention, provided is a method of preparing the superabsorbent polymer having SE of 0.05%/mm or less, as calculated by Equation 1.

In detail, the method of preparing the superabsorbent polymer may include the steps of performing crosslinking polymerization of a monomer mixture including water-soluble ethylene-based unsaturated monomers having at least partially neutralized acidic groups, in the presence of an internal crosslinking agent to form a water-containing gel polymer; drying, pulverizing, and size-sorting the water-containing gel polymer to form a base resin powder; and additionally crosslinking the surface of the base resin powder in the presence of a surface crosslinking agent to form a surface-crosslinked layer, wherein in the step of forming the water-containing gel polymer, the internal crosslinking agent is used in an amount of 0.1 to 0.5 parts by weight, based on 100 parts by weight of the water-soluble ethylene-based unsaturated monomers before neutralization of the acidic groups of the monomers having the acidic groups included in the water-soluble ethylene-based unsaturated monomers, in the step of forming the surface-crosslinked layer, a heating time taken to heat from a temperature of 60° C. to 80° C. to a temperature of 180° C. to 200° C. is controlled from 5 min to 1 hr, and the temperature is maintained at 180° C. to 200° C. for 10 min to 40 min while heating the base resin powder, in the step of forming the surface-crosslinked layer, alumina is added, or after the step of forming the surface-crosslinked layer, alumina is added, or in the step of forming the surface-crosslinked layer, alumina is added and after the step of forming the surface-crosslinked layer, alumina is further added.

The water-soluble ethylene-based unsaturated monomers may include one or more selected from the group consisting of an anionic monomer such as (meth)acrylic acid, maleic acid, maleic anhydride, fumaric acid, crotonic acid, itaconic acid, sorbic acid, vinyl phosphonic acid, vinyl sulfonic acid, allyl sulfonic acid, 2-(meth)acryloylethane sulfonic acid, 2-(meth)acryloyloxyethane sulfonic acid, 2-(meth)acryloyl propane sulfonic acid, or 2-(meth)acrylamido-2-methyl propane sulfonic acid, and salts thereof; a nonionic hydrophilic monomer such as (meth)acrylamide, N-substituted (meth)acrylamide, 2-hydroxyethyl(meth)acrylate, 2-hydroxypropyl(meth)acrylate, methoxy polyethylene glycol(meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof.

The term 'water-soluble ethylene-based unsaturated monomers having at least partially neutralized acidic groups', as used herein, means that monomers having acidic groups are included in the water-soluble ethylene-based unsaturated monomers, and at least part of the acidic groups of the monomers having acidic groups is neutralized.

In particular, the water-soluble ethylene-based unsaturated monomers may be composed of monomers (salts of anionic monomers) in which acidic groups included in anionic monomers are at least partially neutralized.

More specifically, acrylic acid or salts thereof may be used as the water-soluble ethylene-based unsaturated monomer. When acrylic acid is used, acrylic acid which is at least partially neutralized may be used. It is possible to prepare a superabsorbent polymer having superior physical properties by using these monomers. For example, when the alkali metal salt of acrylic acid is used as the water-soluble ethylene-based unsaturated monomer, acrylic acid may be used after being neutralized with a neutralizer such as caustic soda (NaOH). In this regard, a neutralization degree of the acrylic acid may be controlled in the range of about 50 mol % to about 95 mol % or about 60 mol % to about 85 mol %. When the acrylic acid is neutralized within the above range, it is possible to provide a superabsorbent polymer having excellent centrifuge retention capacity without concern about precipitation.

In the monomer mixture including the water-soluble ethylene-based unsaturated monomers, a concentration of the water-soluble ethylene-based unsaturated monomer may be about 20% by weight to about 60% by weight, or about 25% by weight to about 50% by weight, based on a total weight of the monomer mixture including after-mentioned raw materials, internal crosslinking agent, initiator, solvent, additive, etc., and the concentration may be properly controlled, in consideration of a polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be deteriorated.

The internal crosslinking agent is included in the monomer mixture for crosslinking polymerization of the water-soluble ethylene-based unsaturated monomers. The internal crosslinking agent is composed of a compound having two or more crosslinkable functional groups in the molecule. The internal crosslinking agent may include carbon-carbon double bonds as crosslinkable functional groups to facilitate crosslinking polymerization of the above-described water-soluble ethylene-based unsaturated monomers. More specific examples of the internal crosslinking agent may include one or more selected from the group consisting of polyethylene glycol diacrylate (PEGDA), glycerin diacrylate, glycerin triacrylate, non-modified or ethoxylated trimethylol propane triacrylate (TMPTA), hexanediol diacrylate, and triethylene glycol diacrylate.

To provide the superabsorbent polymer showing the above-described absorption properties, it is necessary to control the crosslinking density of the base resin before surface-crosslinking. Specifically, when centrifuge retention capacity (CRC) in the physiological saline solution of the base resin powder prepared by the step of forming the base resin powder described below is controlled from 34 g/g to 35.8 g/g, it is possible to prove the superabsorbent polymer showing balanced absorption properties and excellent anti-rewetting property after surface-crosslinking. The centrifuge retention capacity (CRC) of the base resin in the physiological saline solution may be calculated by putting a value, which is measured by using the base resin instead of the superabsorbent polymer in the above-described method, into Calculation Formula 1.

To control the crosslinking density of the base resin within the above range, the internal crosslinking agent may be used in an amount of 0.1 parts by weight to 0.5 parts by weight or 0.3 parts by weight to 0.5 parts by weight, based on 100 parts by weight of the water-soluble ethylene-based unsaturated monomers.

In this regard, the content of the water-soluble ethylene-based unsaturated monomers is based on the weight of the water-soluble ethylene-based unsaturated monomers before neutralization of the acidic groups of the monomers having the acidic groups which are included in the water-soluble ethylene-based unsaturated monomers. For example, when the water-soluble ethylene-based unsaturated monomers include acrylic acid, the content of the internal crosslinking agent may be controlled, based on the weight of the monomers before neutralization of acrylic acid.

Further, the internal crosslinking agent is included in an amount of about 0.01% by weight to about 2% by weight, based on the monomer mixture, thereby forming the crosslinked polymer showing a rapid absorption rate while having excellent centrifuge retention capacity and absorbency under load.

The monomer mixture may further include a foaming agent and/or a surfactant in order to obtain balanced absorption properties by forming an appropriate pore structure in the superabsorbent polymer.

As the foaming agent, carbonate which stably generates bubbles by a surfactant may be used. More specific examples of the carbonate may include one or more selected from the group consisting of magnesium carbonate, calcium carbonate, sodium bicarbonate, sodium carbonate, potassium bicarbonate, and potassium carbonate.

The foaming agent may be used in an amount of 0.05 parts by weight to 0.5 parts by weight, based on 100 parts by weight of the water-soluble ethylene-based unsaturated monomers. In this regard, the content of the water-soluble ethylene-based unsaturated monomers is also based on the weight of the water-soluble ethylene-based unsaturated monomers before neutralization of the acidic groups of the monomers having the acidic groups which are included in the water-soluble ethylene-based unsaturated monomers. The foaming agent may be used in an amount of about 0.001% by weight to about 0.1% by weight, based on the monomer mixture.

Within this range, the crosslinked polymer showing a rapid absorption rate while having excellent centrifuge retention capacity and absorbency under load may be formed.

As the surfactant, alkyl sulfate salts having 8 to 24 carbon atoms and sugar ester-based surfactants may be used. Specific examples of the alkyl sulfate salt may include sodium dodecyl sulfate, sodium higher alcohol sulfate, sodium lauryl sulfate, lauryl sulfate triethanolamine, etc., and specific examples of the sugar ester-based surfactant may include sucrose monostearate, sucrose monopalmitate, etc. Of them, when sodium dodecyl sulfate is used, discoloration upon drying the water-containing gel polymer and surface-crosslinking the base resin powder may be minimized.

The surfactant may be used in an amount of 0.005 parts by weight to 0.1 parts by weight, based on 100 parts by weight of the water-soluble ethylene-based unsaturated monomers. In this regard, the content of the water-soluble ethylene-based unsaturated monomers is also based on the weight of the water-soluble ethylene-based unsaturated monomers before neutralization of the acidic groups of the monomers having the acidic groups which are included in the water-soluble ethylene-based unsaturated monomers. The surfactant may be used in an amount of about 0.0001% by weight to about 0.01% by weight, based on the monomer mixture. Within this range, foaming efficiency of the foaming agent may be improved, thereby forming the crosslinked polymer having an appropriate pore structure.

Further, the monomer mixture may further include a polymerization initiator which is commonly used in the preparation of superabsorbent polymers.

Specifically, the polymerization initiator may be suitably selected depending on a polymerization method. When a thermal polymerization method is employed, a thermal polymerization initiator is used. When a photo-polymerization method is employed, a photo-polymerization initiator is used. When a hybrid polymerization method (a method of using both heat and light) is employed, both the thermal polymerization initiator and the photo-polymerization initiator may be used. However, even though the photo-polymerization is performed, a certain amount of heat may be generated by light irradiation such as UV irradiation, etc., and also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, specific examples of acyl phosphine may include diphenyl(2,4,6-trimethylbenzoyl)phosphine oxide, phenylbis(2,4,6-trimethylbenzoyl) phosphine oxide, ethyl(2,4,6-trimethylbenzoyl)phenylphosphinate, etc. More various photo-polymerization initiators are well disclosed in "UV Coatings: Basics, Recent Developments and New Application (Elsevier, 2007)" written by Reinhold Schwalm, p 115, however, they are not limited to the above described examples.

The photo-polymerization initiator may be included in an amount of about 0.0001% by weight to about 1.0% by weight with respect to the monomer mixture. If the concentration of the photo-polymerization initiator is too low, the polymerization rate may become low. If the concentration of the photo-polymerization initiator is too high, a molecular weight of the superabsorbent polymer may become low and its physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$), etc. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitrile, 2,2-azobis(2-[2-imidazolin-2-yl]propane)dihydrochloride, 4,4-azobis-(4-cyanovaleric acid), etc. More various thermal polymerization initiators are well-disclosed in 'Principle of Polymerization (Wiley, 1981)' written by Odian, p 203, however, they are not limited to the above described examples.

The thermal polymerization initiator may be included in an amount of about 0.001% by weight to about 1.0% by weight with respect to the monomer mixture. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may become low and its physical properties may not be uniform.

The monomer mixture may further include an additive such as a thickener, a plasticizer, a preservation stabilizer, an antioxidant, etc., if necessary.

The raw materials such as the above-described water-soluble ethylene-based unsaturated monomers, polymerization initiators, internal crosslinking agent, and additive may be prepared in the form of being dissolved in a solvent.

In this regard, as the solvent, any solvent may be used without limitations in the constitution as long as it is able to dissolve the above ingredients, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

The solvent may be included in a remaining amount excluding the above described components from the total weight of the monomer mixture.

The method of forming the water-containing gel polymer by polymerizing the monomer mixture may be controlled such that the polymer before surface-crosslinking (the base resin powder of the present invention) may exhibit centrifuge retention capacity (CRC) of 34 g/g to 35.8 g/g in a physiological saline solution, as described above. As long as the base resin powder showing the above-described centrifuge retention capacity is obtained, various polymerization methods known in the art to which the present invention pertains may be used as the method of forming the water-containing gel polymer.

Specifically, the polymerization method is largely classified into the thermal polymerization and the photo-polymerization according to the polymerization energy source. The thermal polymerization may be commonly carried out in a reactor like a kneader equipped with agitating spindles. In this regard, a polymerization temperature of the monomer mixture is controlled from about 30° C. to about 110° C., thereby forming the water-containing gel polymer having an appropriate crosslinking structure. A means for achieving the polymerization temperature of the above range is not particularly limited. Heating may be performed by providing a heating medium or by directly providing a heat source. A type of the heating medium applicable may be a hot fluid such as steam, hot air, hot oil, etc., but is not limited thereto. The temperature of the heating medium provided may be properly selected in consideration of the means of the heating medium, a heating speed, and a target temperature of heating. Meanwhile, an electric heater or a gas heater may be used as the heat source provided directly, but the heat source is not limited to these examples.

In contrast, the photo-polymerization may be carried out in a reactor equipped with a movable conveyor belt. However, the above-described polymerization method is illustrative, and the present invention is not limited to the polymerization method.

For example, when the thermal polymerization is carried out by providing the heating medium to the reactor like a kneader equipped with the agitating spindles as described above or by heating the reactor, the water-containing gel polymer which is discharged from the outlet of the reactor may be obtained. The water-containing gel polymer thus obtained may have the size of centimeters or millimeters, according to the type of agitating spindles equipped in the reactor. Specifically, the size of the obtained water-containing gel polymer may vary according to a concentration of the monomer mixture fed thereto, a feeding speed, etc.

In addition, when the photo-polymerization may be carried out in the reactor equipped with the movable conveyor belt as described above, the water-containing gel polymer generally obtained may be a water-containing gel polymer in a sheet-type having a width of the belt. In this regard, a thickness of the polymer sheet may vary according to the concentration of the monomer mixture fed thereto and the feeding speed, and the monomer mixture is preferably fed such that the polymer sheet having a thickness of about 0.5 cm to about 10 cm is obtained. If the monomer mixture is fed such that the thickness of the sheet-type polymer becomes too thin, the production efficiency becomes low, which is not preferred. If the thickness of the sheet-type polymer exceeds 10 cm, the polymerization reaction may not uniformly occur throughout the polymer due to the excessively high thickness.

A polymerization time of the monomer mixture may be controlled according to the polymerization method which is used to allow the base resin powder obtained in a subsequent process to have the above-described centrifuge retention capacity. For non-limiting example, the polymerization time of the monomer mixture may be controlled from about 30 sec to about 60 min, thereby preparing the base resin powder having the above-described centrifuge retention capacity.

The water-containing gel polymer thus obtained by the method may have generally a water content of about 30% by weight to about 80% by weight. Meanwhile, the term "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 40 minutes, including 5 minutes for the temperature rising step.

After crosslinking polymerization of the monomers, drying, pulverizing, and size-sorting processes may be performed to obtain the base resin powder. Through the pulverizing and size-sorting processes, the base resin powder and the superabsorbent polymer obtained therefrom are suitably prepared and provided such that they have a particle size of about 150 μm to about 850 μm. More specifically, at least about 95% by weight of the base resin powder and the superabsorbent polymer obtained therefrom may have a particle size of about 150 μm to about 850 μm, and fine powder having a particle size of less than about 150 μm may be less than about 3% by weight.

As such, when particle size distributions of the base resin powder and the superabsorbent polymer are controlled within the preferred range, the superabsorbent polymer finally prepared may exhibit excellent absorption properties.

Meanwhile, the methods of performing the drying, pulverizing, and size-sorting will be described in more detail as follows.

First, in drying the water-containing gel polymer, a coarse pulverization process may be further carried out before drying in order to increase the efficiency of the drying process, if necessary.

There is no limitation in the constitution of a milling machine to be used. Specifically, any one device selected from the group consisting of a vertical pulverizer, a turbo cutter, a turbo grinder, a rotary cutter mill, a cutter mill, a disc mill, a shred crusher, a crusher, a chopper, and a disc cutter may be used, but it is not limited thereto.

In this regard, the coarse pulverization may be carried out such that the water-containing gel polymer has a particle size of about 0.2 mm to about 15 mm.

Due to the high water content, it is technically not easy to pulverize the water-containing gel polymer into a particle size of less than 0.2 mm, and a phenomenon of agglomeration between the pulverized particles may occur. Meanwhile, when the particle size is larger than 15 mm, the effect of increasing the efficiency of the subsequent drying process may be unsatisfactory.

The water-containing gel polymer coarsely pulverized as above or the water-containing gel polymer immediately after polymerization without the coarse pulverizing step is subjected to drying. In this regard, a drying temperature of the drying step may be about 50° C. to about 250° C.

When the drying temperature is lower than 50° C., it is likely that the drying time becomes too long or the physical properties of the superabsorbent polymer finally formed are deteriorated, and when the drying temperature is higher than 250° C., only the surface of the polymer is dried, and thus it is likely that fine powder is generated during the subsequent pulverizing step and the physical properties of the superabsorbent polymer finally formed are deteriorated.

Meanwhile, the drying time may be about 20 minutes or about 15 hours, in consideration of process efficiency, etc., but is not limited thereto.

The drying method of the drying step may also be selected and used without any limitation in the constitution, as long as it is a method generally used for drying the water-containing gel polymer. Specifically, the drying step may be carried out by a method such as hot air supply, infrared irradiation, microwave irradiation, or ultraviolet irradiation. When the drying step as above is finished, the water content of the polymer may be about 0.1% by weight to about 10% by weight.

Subsequently, the dried polymer obtained through the drying step is subjected to a pulverization step.

The polymer powder obtained through the pulverizing step may have a particle size of about 150 μm to about 850 μm. Specific examples of a milling machine used to achieve the above particle size may include a pin mill, a hammer mill, a screw mill, a roll mill, a disc mill, a jog mill, etc., but is not limited thereto.

Also, in order to manage the physical properties of the superabsorbent polymer powder finally commercialized after the pulverization step, a separate process of sorting the polymer powder obtained after the pulverization depending on the particle size may be performed. Preferably, a polymer having a particle size of about 150 μm to about 850 μm is sorted, and only the polymer powder having such a particle size is subjected to the surface crosslinking reaction and finally commercialized. A particle size distribution of the base resin powder obtained through this process has been described, and a specific description thereof will be omitted.

The base resin powder obtained by the step of forming the base resin powder may have centrifuge retention capacity (CRC) of 34 g/g to 35.8 g/g in a physiological saline solution, as described above. The base resin powder showing the centrifuge retention capacity may exhibit superior absorption properties while showing excellent centrifuge retention capacity through the subsequent surface-crosslinking process, and therefore, SE of Equation 1 may be 0.05%/mm or less.

Meanwhile, after the process of forming the above-described base resin powder, the surface of the base resin powder may be further crosslinked in the presence of the surface crosslinking agent to form the surface-crosslinked layer, thereby preparing the superabsorbent polymer.

The surface-crosslinked layer may be formed by using a surface crosslinking agent which has been used in the preparation of superabsorbent polymers. As the surface crosslinking agent, any surface crosslinking agent known in the art to which the present invention pertains may be used without limitation. More specific examples thereof may include polyols such as ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, etc., or carbonate-based compounds such as ethylene carbonate, propylene carbonate, etc. Such surface crosslinking agent may be used in an amount of about 0.01 parts by weight to 3 parts by weight with respect to 100 parts by weight of the base resin powder.

The preparation method may provide the superabsorbent polymer having SE of Equation 1 of 0.05%/mm or less by adding alumina in the surface-crosslinking process, or by adding alumina after the surface-crosslinking process, or by adding alumina in the surface-crosslinking process and then by adding alumina after the surface-crosslinking process.

The alumina may be used in a powdery form or in a liquid form. The alumina may be used in an amount of about 0.01 parts by weight to about 0.2 parts by weight, based on 100 parts by weight of the base resin powder, thereby providing the superabsorbent polymer having low SE of Equation 1.

Further, in the surface crosslinking process, when the surface crosslinking is performed by adding a multivalent metal cation as needed, the surface crosslinked structure of the superabsorbent polymer may be further optimized. This may be because the metal cation forms a chelate with a carboxyl group (COOH) of the superabsorbent polymer to further reduce a crosslinking distance.

Further, there are no limitations in the method of adding the surface crosslinking agent, inorganic compound, or multivalent metal cation as needed to the base resin powder. For example, a method of spraying the surface crosslinking agent onto the base resin powder and the inorganic compound while stirring the base resin powder and the inorganic compound may be used.

When the surface crosslinking agent is added, any one of water and methanol may be further added alone or a mixture thereof may be further added. When water and/or methanol are/is added, there is an advantage that the surface crosslinking agent may be evenly distributed in the base resin powder. At this time, amount(s) of water and/or methanol to be added may be regulated for the purposes of inducing a uniform dispersion of the surface crosslinking agent, preventing an agglomeration phenomenon of the base resin powder, and optimizing a surface penetration depth of the surface crosslinking agent.

In the step of forming the surface-crosslinked layer, the base resin powder is heated under appropriate conditions, thereby providing the superabsorbent polymer having low SE of Equation 1.

Specifically, while heating the base resin powder, a heat-up time from the reaction initiation temperature to the maximum reaction temperature may be controlled to about 5 min to about 1 hr, and the maximum reaction temperature may be maintained for 10 min to 40 min, thereby providing the superabsorbent polymer having low SE of Equation 1. In this regard, the reaction initiation temperature may be controlled from about 60° C. to about 80° C., and the maximum reaction temperature may be controlled from about 180° C. to about 200° C. The above temperature may be a temperature of the reactant (i.e., the base resin) or the reactor where surface-crosslinking reaction is performed. For example, the reaction initiation temperature may refer to the temperature of the reactant (i.e., the base resin) when the surface-crosslinking reaction is initiated, and the maximum reaction temperature may refer to the highest temperature of the reactor during the surface-crosslinking reaction.

A heating means for surface crosslinking reaction is not particularly limited, and the heating means used for polymerization of the monomer mixture may be used.

Hereinafter, the actions and effects of the present invention will be described in more detail with reference to specific Examples of the present invention. However, these Examples are for illustrative purposes only, and the scope of the present invention is not intended to be limited thereby.

Example 1: Preparation of Superabsorbent Polymer

To a glass reactor, 500 g of acrylic acid, 1.5 g of polyethyleneglycol diacrylate (PEGDA, a molecular weight of 400), 0.5 g of trimethylolpropane triacrylate containing 9 mol % of ethylene oxide (Ethoxylated-TMPTA, TMP(EO)9TA, M-3190 Miwon Specialty Chemical Co., Ltd.), and 0.4 g of IRGACURE 819 were injected. In this regard, a total weight of the used non-neutralized acrylic acid was 500 g, and a total weight of the internal crosslinking agent was 2 g. Thus, the internal crosslinking agent was used in an amount of 0.4 parts by weight with respect to 100 parts by weight of the non-neutralized acrylic acid.

To the glass reactor, 0.05 g of sodium dodecyl sulfate as a surfactant was added and mixed, and then 800 g of a 24% caustic soda solution was slowly added dropwise and mixed. After confirming that the temperature of the mixed solution increased to about 72° C. or higher by neutralization heat upon adding dropwise the caustic soda solution, the mixed solution was left until it was cooled.

When the temperature of the mixed solution was cooled to about 45° C., 0.5 g of sodium bicarbonate was added to the mixed solution and mixed. Subsequently, the obtained composition was subjected to light irradiation for 1 min to perform photo-polymerization reaction. The polymer obtained by the polymerization reaction was passed through a hole having a diameter of 13 mm by using a meat chopper to prepare crumbs.

Subsequently, the crumbs were dried in an oven capable of shifting airflow up and down. The crumbs were uniformly dried by flowing hot air at 180° C. from the bottom to the top for 15 minutes and from the top to the bottom for 15 minutes such that the dried crumbs had a water content of about 2% or less.

The dried crumbs were pulverized using a pulverizer and sorted by size, and a base resin having a size of about 150 μm to about 850 μm was obtained.

To 100 g of the prepared base resin powder, 0.05 g of alumina was added, and stirred at room temperature to uniformly mix the base resin powder and alumina. Subsequently, 0.5 g of ethylene carbonate, 3 g of water, and 3 g of methanol were mixed to prepare a surface-crosslinking solution. Then, the surface-crosslinking solution was sprayed onto the base resin powder, and stirred at room temperature to mix them such that the surface-crosslinking solution was evenly distributed on the base resin powder. Subsequently, the base resin powder mixed with the surface-crosslinking solution was added to a surface-crosslinking reactor, followed by surface-crosslinking reaction.

In the surface-crosslinking reactor, a temperature of the base resin powder was confirmed to gradually increase from an initial temperature around 80° C. The surface-crosslinking reactor was operated such that the temperature reached the maximum reaction temperature of 190° C., after 30 min starting from the initial temperature. After reaching the maximum reaction temperature, the reaction was further allowed for 15 min to obtain a surface-crosslinked superabsorbent polymer. The superabsorbent polymer was pulverized and sorted through an ASTM standard sieve to obtain a superabsorbent polymer having a particle size of 150 μm to 850 μm.

Example 2: Preparation of Superabsorbent Polymer

A surface-crosslinked superabsorbent polymer was prepared in the same manner as in Example 1, except that after reaching the maximum reaction temperature, the surface-crosslinking reaction was further allowed for 30 min in the surface-crosslinking process of Example 1.

Comparative Example 1: Preparation of Superabsorbent Polymer

A surface-crosslinked superabsorbent polymer was prepared in the same manner as in Example 1, except that polyethyleneglycol diacrylate and trimethylolpropane triacrylate containing 9 mol % of ethylene oxide were used in an amount of 3.0 g and 1.0 g, respectively in Example 1. According to Comparative Example 1, a total weight of the used non-neutralized acrylic acid was 500 g, and a total weight of the internal crosslinking agent was 4 g. Thus, the internal crosslinking agent was used in an amount of 0.8 parts by weight with respect to 100 parts by weight of the non-neutralized acrylic acid.

Comparative Example 2: Preparation of Superabsorbent Polymer

A surface-crosslinked superabsorbent polymer was prepared in the same manner as in Example 1, except that after reaching the maximum reaction temperature, the surface-crosslinking reaction was further allowed for 50 min in the surface-crosslinking process of Example 1.

Comparative Example 3: Preparation of Superabsorbent Polymer

A surface-crosslinked superabsorbent polymer was prepared in the same manner as in Example 1, except that 0.05 g of aerosil 200 (EVONIK) was added instead of 0.05 g of alumina in Example 1.

Experimental Example 1: Evaluation of Properties of Superabsorbent Polymers

Properties of the base resins and the superabsorbent polymers prepared according to Examples and Comparative Examples were evaluated by the following methods, and shown in the following Table 1.

(1) Centrifuge Retention Capacity (CRC)

Centrifuge retention capacity (CRC) in a physiological saline solution was measured for the base resins and the superabsorbent polymers of Examples and Comparative Examples in accordance with EDANA method WSP 241.2.

In detail, among the base resins and the superabsorbent polymers to be tested for centrifuge retention capacity, those having a particle size of 150 μm to 850 μm, which were passed through a US standard 20 mesh screen and retained on a US standard 100 mesh screen, were prepared as samples.

The sample $W_0$ (g, about 0.2 g) having a particle size of 150 μm to 850 μm was uniformly placed into a non-woven fabric bag, followed by sealing. Then, the bag was immersed into 0.9% by weight of a physiological saline solution at room temperature. 30 minutes later, the bag was drained at 250 G for 3 minutes with a centrifuge, and the weight $W_2(g)$ of the bag was then measured. Meanwhile, the same procedure was carried out using an empty bag having no sample, and the resultant weight $W_1(g)$ was measured.

Each of the weights thus obtained was used to confirm centrifuge retention capacity according to the following Calculation Formula 1:

$$\text{CRC (g/g)} = \{[W_2(g) - W_1(g)]/W_0(g)\} - 1 \quad \text{[Calculation Formula 1]}$$

wherein $W_0(g)$ represents an initial weight (g) of the sample having a particle size of 150 μm to 850 μm, $W_1(g)$ represents a weight of an empty non-woven fabric bag, which was measured after immersing the empty non-woven fabric bag containing no sample in 0.9% by weight of a physiological saline solution at room temperature for 30 minutes, and dehydrating the non-woven fabric bag using a centrifuge at 250 G for 3 minutes, and $W_2(g)$ represents a weight of the non-woven fabric bag containing the sample, which was measured after immersing the non-woven fabric bag containing the sample in 0.9% by weight of a physiological saline solution at room temperature for 30 minutes, and dehydrating the non-woven fabric bag using a centrifuge at 250 G for 3 minutes.

(2) Absorbency Under Load (AUL)

Absorbency under load (AUL) of 0.9 psi in the physiological saline solution was measured for the superabsorbent polymers in accordance with EDANA method WSP 242.2.

In detail, a 400 mesh stainless steel net was installed in the bottom of a plastic cylinder having an internal diameter of 25 mm. The superabsorbent polymer $W_0$ (g, 0.16 g) to be tested for absorbency under load was uniformly scattered on the screen at room temperature and humidity of 50%. Subsequently, a piston which may uniformly provide a load of 6.3 kPa (0.9 psi) was put thereon, in which an external diameter of the piston was slightly smaller than 25 mm, there was no gab between the internal wall of the cylinder and the piston, and the jig-jog of the cylinder was not interrupted. At this time, the weight $W_3(g)$ of the apparatus was measured. After putting a glass filter having a diameter of 90 mm and a thickness of 5 mm in a petri dish having a diameter of 150 mm, 0.9% by weight of a sodium chloride aqueous solution (physiological saline solution) was poured in the petri dish until the surface level of the physiological saline solution became equal to the upper surface of the glass filter. A sheet of filter paper having a diameter of 90 mm was put on the glass filter.

Subsequently, the prepared apparatus was put on the filter paper and the superabsorbent polymer in the apparatus was allowed to swell by the physiological solution under a load.

After 1 hr, the weight $W_4(g)$ of the apparatus containing the swollen superabsorbent polymer was measured.

The weights thus obtained were used to calculate absorbency under load according to the following Calculation Formula 2:

$$AUL\ (g/g)=[W_4(g)-W_3(g)]/W_0(g) \quad \text{[Calculation Formula 2]}$$

wherein $W_0(g)$ represents an initial weight (g) of the superabsorbent polymer, $W_3(g)$ represents the sum of the weight of the superabsorbent polymer and the weight of the apparatus capable of providing a load for the superabsorbent polymer, and $W_4(g)$ represents the sum of the weight of the superabsorbent polymer after allowing the superabsorbent polymer to absorb the physiological saline solution under a load (0.9 psi) for 1 hour, and the weight of the apparatus capable of providing the load for the superabsorbent polymer.

(3) Gel Bed Permeability (GBP)

Free swell gel bed permeability (GBP) in a physiological saline solution was measured for the superabsorbent polymers in accordance with the following method described in Patent Application No. 2014-7018005.

In detail, an apparatus illustrated in FIGS. 2 to 4 was used to conduct a free swell GBP test. First, a plunger 536, with a weight 548 seated thereon, was placed in an empty sample container 530 and the height from the top of the weight 548 to the bottom of the sample container 530 was measured using a suitable gauge accurate to 0.01 mm. The force the thickness gauge applies during measurement was controlled to less than about 0.74 N.

Meanwhile, among the superabsorbent polymers to be tested for GBP, superabsorbent polymers, which were passed through a US standard 30 mesh screen and retained on a US standard 50 mesh screen, were selected to obtain the superabsorbent polymer having a particle size of 300 μm to 600 μm.

About 2.0 g of the size-sorted superabsorbent polymer was placed in the sample container 530 and spread out evenly on the bottom of the sample container. This container without the plunger 536 and weight 548 therein was then submerged in the 0.9% by weight of a physiological saline solution for about 60 minutes to allow the superabsorbent polymer to swell free of any restraining load. At this time, the sample container 530 was set on a mesh located in a liquid reservoir so that the sample container 530 was raised slightly above the bottom of a liquid reservoir. The mesh did not inhibit the flow of the physiological saline solution into the sample container 530. During saturation, a depth of the physiological saline solution was controlled such that the surface within the sample container was defined solely by the swollen superabsorbent polymer, rather than the physiological saline solution.

At the end of this period, an assembly of the plunger 536 and the weight 548 was placed on the swollen superabsorbent polymer 568 in the sample container 530, and then the sample container 530, plunger 536, weight 548, and swollen superabsorbent polymer 568 were removed from the solution. Then, before GBP measurement, the sample container 530, plunger 536, weight 548, and swollen superabsorbent polymer 568 were to remain at rest for about 30 seconds on a large grid non-deformable plate of uniform thickness. The height from the top of the weight 548 to the bottom of the sample container 530 was measured again by using the same thickness gauge used previously. The height measurement of the apparatus where the plunger 536 and the weight 548 were placed in the empty sample container 530 was subtracted from the height measurement of the apparatus containing the swollen superabsorbent polymer 568 to obtain the thickness or height "H" of the swollen superabsorbent polymer.

For GBP measurement, a flow of 0.9% physiological saline solution was delivered into the sample container 530 with the swollen superabsorbent polymer 568, plunger 536, and weight 548 inside. The flow rate of the physiological saline solution into the sample container 530 was adjusted to cause the physiological saline solution to overflow the top of the cylinder 534, resulting in a consistent head pressure equal to the height of the sample container 530. The quantity of solution passing through the swollen superabsorbent polymer 568 versus time was measured gravimetrically using a scale 602 and a beaker 603. Data points from the scale 602 were collected every second for at least 60 seconds once the overflow has begun. The flow rate, Q through the swollen superabsorbent polymer 568 was determined in units of g/sec by a linear least-square fit of fluid (g) passing through the swollen superabsorbent polymer 568 versus time (sec).

GBP ($cm^2$) was calculated from the obtained data according to the following Calculation Formula 3:

$$K=[Q*H*\mu]/[A*\rho*P] \quad \text{[Calculation Formula 3]}$$

wherein K is gel bed permeability ($cm^2$),

Q is a flow rate (g/sec),

H is a height of swollen superabsorbent polymer (cm),

μ is liquid viscosity (P) (viscosity of the physiological saline solution used in this test was about 1 cp), A is a cross-sectional area for liquid flow (28.27 $cm^2$ for the sample container used in this test), ρ is a liquid density ($g/cm^3$) (about 1 $g/cm^3$ for the physiological saline solution used in this test), and P is a hydrostatic pressure ($dynes/cm^2$) (normally about 7,797 $dynes/cm^2$).

The hydrostatic pressure is calculated from $P=\rho*g*h$, wherein p is a liquid density ($g/cm^3$), g is gravitational acceleration (nominally 981 $cm/sec^2$), and h is a fluid height (e.g., 7.95 cm for the GBP test described herein).

At least two samples were tested, and an average of the results was determined as free swell GBP of the superabsorbent polymer, and the unit was converted to darcy (1 darcy=0.98692×$10^{-8}$ $cm^2$) and shown in Table 1.

(4) Absorption Rate (Vortex Time) of Superabsorbent Polymer

The absorption rates of the superabsorbent polymers were measured in seconds in accordance with a method described in International Patent Application No. 1987-003208.

In detail, the absorption rate (or vortex time) was calculated by measuring a time in seconds which was required until the vortex disappears, after adding 2 g of the polymer to 50 mL of 0.9% by weight of a sodium chloride aqueous solution (physiological saline solution) and then agitating it at 600 rpm. At this time, as a stirring bar, a stirring bar having a size of 31.8 mm×8 mm (manufacturer: Bel Art) was used.

(5) % Saline Extracted (SE) from Empty Spaces of Swollen Superabsorbent Polymer

The amount of saline remaining in the empty spaces between swollen superabsorbent polymers was confirmed according to the following method.

A cylinder having a diameter of 6 cm and a thickness of 5 mm was put in a petri dish, 2 g of the superabsorbent polymer was evenly distributed in the cylinder, a piston which may uniformly provide a load of 0.02 psi was put thereon. As shown in FIG. 1, an inlet was formed in the piston, and therefore, a physiological saline solution may be injected while applying a load to the superabsorbent polymer. Subsequently, 20 g of a physiological saline solution (0.9% by weight of a sodium chloride aqueous solution) was injected into the inlet of the piston to swell the superabsorbent polymer. 15 minutes later, a piston which may uniformly provide a load of 0.40 psi was additionally put on the previous piston, 20 g of the physiological saline solution is additionally injected into the inlet of the piston, and 15 minutes later, the height (unit: mm) of the swollen superabsorbent polymer is measured. In this regard, the height of the swollen superabsorbent polymer was determined by measuring the shortest distance from the bottom of the cylinder to the borderline between the superabsorbent polymer and the piston while maintaining the two pistons previously put thereon.

After measuring the height of the swollen superabsorbent polymer, the physiological saline solution was extracted for 1 min from the swollen superabsorbent polymer by using a vacuum pump (product name: DA-30D, manufacturer: ULVAC) under vacuum of 5 psi to calculate a weight change $\Delta w$ (g) before and after extraction. The height of the swollen superabsorbent polymer and the calculated weight change were put into the following Equation 1 to calculate % saline extracted (SE) from the empty spaces of the swollen superabsorbent polymer:

$$SE = \frac{\Delta w}{w_t \times h} \times 100 \quad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which may uniformly provide a load of 0.02 psi is put thereon, 20 g of a physiological saline solution (0.9% by weight of a sodium chloride aqueous solution) is injected into the inlet of the piston, and 15 minutes later, a piston which may uniformly provide a load of 0.40 psi is additionally put thereon, 20 g of the physiological saline solution is additionally injected into the inlet of the piston, and 15 minutes later, the height of the swollen superabsorbent polymer is measured, $w_t$ represents a total weight (g) of the physiological saline solution injected into the superabsorbent polymer, and $\Delta w$ represents a weight change (g) before and after extraction, which is calculated by extracting the physiological saline solution from the swollen superabsorbent polymer for 1 minute under vacuum of 5 psi by using a vacuum pump, after measuring the height of the swollen superabsorbent polymer.

Experimental Example 2: Evaluation of Properties of Diaper

In order to confirm that as the amount of saline extracted from the empty spaces between the swollen superabsorbent polymers is smaller, a rewetting property is more excellent, the superabsorbent polymer having low SE of Examples 1 and 2, and superabsorbent polymer having high SE of Comparative Examples 1 to 3 were used to manufacture diaper samples, and their rewetting properties were tested and shown in the following Table 2.

(1) Manufacture of Diaper Samples

The superabsorbent polymers were size-sorted into a particle having a particle size of about 600 μm to about 850 μm (size-sorted by using US standard 20 mesh and 30 mesh screens), a particle having a particle size of about 300 μm to about 600 μm (size-sorted by using US standard 30 mesh and 50 mesh screens), and a particle having a particle size of about 90 μm to about 300 μm (size-sorted by using US standard 50 mesh and 170 mesh screens) in a weight ratio of 10:70:20.

The superabsorbent polymers thus size-sorted were used to manufacture diaper samples, in which a core of the diaper was composed of 70% by weight of the superabsorbent polymer and 30% by weight of fluff, and ADL (acquisition/distribution layer) and a top cover were laminated on the core.

(2) Rewetting Properties of Diapers

The rewetting properties of the diapers were evaluated according to a method developed by Kimberly clark, in which the method is used to test the rewetting property under no load or under a load.

In detail, to test the rewetting property under a load, 85 mL of 0.9% by weight of a sodium chloride aqueous solution (a physiological saline solution) was injected into the diapers, and a weight capable of uniformly providing a load of 0.02 psi was put on the physiological saline solution-injected diaper. 15 min later, a weight capable of uniformly providing a load of 0.40 psi was additionally put on the diaper. While providing a total of 0.42 psi load, 85 mL of the physiological saline solution was injected again. 15 min later, the weight on the diaper was removed for a while, and then a paper of 30 cm×10 cm was put on the diaper. Then, the weight was put on the paper again, resulting in interposition of the paper between the diaper and the weight. 2 min later, the amount of saline soaked by the paper from the diaper was measured, and the rewetting amount (g) was calculated by the following Calculation Formula 4:

Rewetting amount$(g)=W_6(g)-W_5(g)$  [Calculation Formula 4]

wherein $W_5(g)$ represents an initial weight of the paper, and $W_6(g)$ represents the weight of the paper that absorbed

TABLE 1

|  | Example 1 | Example 2 | Comparative Example 1 | Comparative Example 2 | Comparative Example 3 |
|---|---|---|---|---|---|
| CRC [g/g] of base resin | 34.5 | 34.5 | 30.5 | 34.5 | 34.5 |
| CRC [g/g] of superabsorbent polymer | 31.8 | 31.5 | 28.0 | 29.0 | 31.5 |
| AUL [g/g] | 19.3 | 20.5 | 18.0 | 18.5 | 18.0 |
| GBP [darcy] | 56 | 53 | 50 | 52 | 49 |
| Vortex time [sec] | 49 | 49 | 50 | 55 | 50 |
| SE [%/mm] | 0.03 | 0.04 | 0.13 | 0.18 | 0.09 | liquid which oozed from the diaper under a load (0.42 psi) for 2 min after injecting the physiological saline solution into the diaper under a load.

TABLE 2

|  | Example 1 | Example 2 | Comparative Example 1 | Comparative Example 2 | Comparative Example 3 |
|---|---|---|---|---|---|
| SE [%/mm] | 0.03 | 0.04 | 0.11 | 0.18 | 0.09 |
| Rewetting amount [g] | 11.9 | 13.2 | 20.4 | 26.1 | 19.6 |

Referring to Table 2, when the superabsorbent polymers of Examples having a small amount of saline remaining in the empty spaces between the swollen gel particles were used, more excellent rewetting properties were observed, as compared with the superabsorbent polymers of Comparative Examples.

REFERENCE NUMERALS

500: GBP measuring apparatus
528: Test apparatus assembly
530: Sample container
534: Cylinder
534a: Region with outer diameter of 66 mm
536: Plunger
538: Shaft
540: O-ring
544, 554, 560: Holes
548: Annular weight
548a: Thru-bore
550: plunger head
562: shaft hole
564: Stainless steel cloth screen of 100 mesh
566: Stainless steel cloth screen of 400 mesh
568: Sample
600: Weir
601: Collection device
602: Scale
603: Beaker
604: Metering pump

The invention claimed is:

1. A superabsorbent polymer, comprising: a base resin powder including a crosslinked polymer which is prepared by crosslinking polymerization of water-soluble ethylene-based unsaturated monomers having at least partially neutralized acidic groups in the presence of an internal crosslinking agent;
a surface-crosslinked layer formed on the base resin powder, wherein the surface-crosslinked layer is obtained by additionally crosslinking the crosslinked polymer in the presence of a surface crosslinking agent, and
alumina in an amount of about 0.01 parts by weight to about 0.2 parts by weight based on 100 parts by weight of the base resin powder,
wherein the superabsorbent polymer has SE (saline extracted) of 0.05%/mm or less, as calculated by the following Equation 1:

$$SE = \frac{\Delta w}{w_t \times h} \times 100 \qquad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which uniformly provides a load of 0.02 psi is put thereon, 20 g of a physiological saline solution is injected into the inlet of the piston, and 15 minutes later, a piston which uniformly provides a load of 0.40 psi is additionally put thereon, 20 g of the physiological saline solution is additionally injected into the inlet of the piston, and 15 minutes later, the height of the swollen superabsorbent polymer is measured,
$w_t$ represents a total weight of the physiological saline solution injected into the superabsorbent polymer, having unit of g, and
$\Delta w$ represents a weight change before and after extraction, having unit of g, which is calculated by extracting the physiological saline solution from the swollen superabsorbent polymer for 1 minute under vacuum of 5 psi by using a vacuum pump, after measuring the height of the swollen superabsorbent polymer.

2. The superabsorbent polymer of claim 1, wherein centrifuge retention capacity in a physiological saline solution is 31 g/g to 40 g/g.

3. The superabsorbent polymer of claim 1, wherein absorbency under load of 0.9 psi in a physiological saline solution is 19 g/g to 25 g/g.

4. The superabsorbent polymer of claim 1, wherein free swell gel bed permeability in a physiological saline solution is 40 darcy to 60 darcy.

5. The superabsorbent polymer of claim 1, wherein a vortex time is 40 sec to 60 sec.

6. A method of preparing a superabsorbent polymer, the method comprising the steps of:
performing crosslinking polymerization of a monomer mixture including water-soluble ethylene-based unsaturated monomers having at least partially neutralized acidic groups, in the presence of an internal crosslinking agent to form a water-containing gel polymer;
drying, pulverizing, and size-sorting the water-containing gel polymer to form a base resin powder; and
additionally crosslinking the surface of the base resin powder in the presence of a surface crosslinking agent to form a surface-crosslinked layer,
wherein in the step of forming the water-containing gel polymer, the internal crosslinking agent is used in an amount of 0.1 parts by weight to 0.5 parts by weight, based on 100 parts by weight of the water-soluble ethylene-based unsaturated monomers before neutralization of the acidic groups of the monomers having acidic groups included in the water-soluble ethylene-based unsaturated monomers,
in the step of forming the surface-crosslinked layer, a heating time taken to heat from a temperature of 60° C. to 80° C. to a temperature of 180° C. to 200° C. is controlled from 5 min to 1 hr, and the temperature is maintained at 180° C. to 200° C. for 10 min to 40 min while heating the base resin powder,
in the step of forming the surface-crosslinked layer, alumina is added, or after the step of forming the surface-crosslinked layer, alumina is added, or in the step of forming the surface-crosslinked layer, alumina is added and after the step of forming the surface-crosslinked layer, alumina is further added, wherein the alumina is included in an amount of about 0.01 parts by weight to about 0.2 parts by weight based on 100 parts by weight of the base resin powder, thereby preparing the superabsorbent polymer having SE of 0.05%/mm or less, as calculated by Equation 1:

$$SE = \frac{\Delta w}{w_t \times h} \times 100 \qquad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which uniformly provides a load of 0.02 psi is put thereon, 20 g of a physiological saline solution is injected into the inlet of the piston, and 15 minutes later, a piston which uniformly provides a load of 0.40 psi is additionally put thereon, 20 g of the physiological saline solution is additionally injected into the inlet of the piston, and 15 minutes later, the height of the swollen superabsorbent polymer is measured, $w_t$ represents a total weight of the physiological saline solution injected into the superabsorbent polymer, having unit of g, and $\Delta w$ represents a weight change before and after extraction, having unit of g, which is calculated by extracting the physiological saline solution from the swollen superabsorbent polymer for 1 minute under vacuum of 5 psi by using a vacuum pump, after measuring the height of the swollen superabsorbent polymer.

7. The method of preparing the superabsorbent polymer of claim 6, wherein the monomer mixture further includes, as a foaming agent, one or more carbonates selected from the group consisting of magnesium carbonate, calcium carbonate, sodium bicarbonate, sodium carbonate, potassium bicarbonate, and potassium carbonate.

8. The method of preparing the superabsorbent polymer of claim 6, wherein the monomer mixture further includes, as a surfactant, one or more selected from the group consisting of alkyl sulfate salts having 8 to 24 carbon atoms and sugar ester-based surfactants.

9. The method of preparing the superabsorbent polymer of claim 6, wherein the base resin powder prepared by the step of forming the base resin powder has centrifuge retention capacity of 34 g/g to 35.8 g/g in a physiological saline solution.

10. The method of preparing the superabsorbent polymer of claim 6, wherein in the step of forming the surface-crosslinked layer, a heating time taken to heat from a reactant temperature of 60° C. to 80° C. to a reactor temperature of 180° C. to 200° C. is controlled from 5 min to 1 hr, and the reactor temperature is maintained at 180° C. to 200° C. for 10 min to 40 min.

11. A superabsorbent polymer, comprising a base resin powder including a crosslinked polymer which is prepared by crosslinking polymerization of water-soluble ethylene-based unsaturated monomers having at least partially neutralized acidic groups in the presence of an internal crosslinking agent;

a surface-crosslinked layer formed on the base resin powder, wherein the surface-crosslinked layer is obtained by additionally crosslinking the crosslinked polymer in the presence of a surface crosslinking agent, and alumina in an amount of about 0.01 parts by weight to about 0.2 parts by weight based on 100 parts by weight of the base resin powder, and wherein the superabsorbent polymer has absorbency under load (AUL) of 0.9 psi of 19 g/g to 25 g/g in a physiological saline solution and SE (saline extracted) of 0.05%/mm or less, as calculated by the following Equation 1:

$$SE = \frac{\Delta w}{w_t \times h} \times 100 \qquad \text{[Equation 1]}$$

wherein h represents a height of the superabsorbent polymer, having unit of mm, which is measured in this manner that a cylinder having a diameter of 6 cm and a thickness of 5 mm is put in a petri dish, 2 g of the superabsorbent polymer is evenly distributed in the cylinder, a piston which uniformly provides a load of 0.02 psi is put thereon, 20 g of a physiological saline solution is injected into the inlet of the piston, and 15 minutes later, a piston which uniformly provides a load of 0.40 psi is additionally put thereon, 20 g of the physiological saline solution is additionally injected into the inlet of the piston, and 15 minutes later, the height of the swollen superabsorbent polymer is measured, $w_t$ represents a total weight of the physiological saline solution injected into the superabsorbent polymer, having unit of g, and $\Delta w$ represents a weight change before and after extraction, having unit of g, which is calculated by extracting the physiological saline solution from the swollen superabsorbent polymer for 1 minute under vacuum of 5 psi by using a vacuum pump, after measuring the height of the swollen superabsorbent polymer.

\* \* \* \* \*